(12) United States Patent
Godager

(10) Patent No.: US 9,400,765 B2
(45) Date of Patent: Jul. 26, 2016

(54) TOOL SERVICE LIFE SENSOR WITH WIRELESS CONNECTIVITY

(75) Inventor: Oivind Godager, Sandefjord (NO)

(73) Assignee: Sensor Development AS, Sandefjord (NO)

( * ) Notice: Subject to any disclaimer, the term of this patent is extended or adjusted under 35 U.S.C. 154(b) by 1088 days.

(21) Appl. No.: 13/513,833

(22) PCT Filed: Nov. 30, 2010

(86) PCT No.: PCT/GB2010/002202
§ 371 (c)(1),
(2), (4) Date: Nov. 15, 2012

(87) PCT Pub. No.: WO2011/067557
PCT Pub. Date: Jun. 9, 2011

(65) Prior Publication Data
US 2013/0090856 A1 Apr. 11, 2013

(30) Foreign Application Priority Data
Dec. 4, 2009 (GB) .................................. 0921340.6

(51) Int. Cl.
| | |
|---|---|
| *G07C 3/00* | (2006.01) |
| *G01V 99/00* | (2009.01) |
| *G06F 17/40* | (2006.01) |
| *G06F 19/00* | (2011.01) |
| *G06F 15/00* | (2006.01) |
| *E21B 41/00* | (2006.01) |
| *G01N 3/58* | (2006.01) |
| *G01V 9/00* | (2006.01) |
| *E21B 47/12* | (2012.01) |

(52) U.S. Cl.
CPC ............... *G06F 15/00* (2013.01); *E21B 41/00* (2013.01); *G01N 3/58* (2013.01); *G01V 9/00* (2013.01); *G07C 3/00* (2013.01); *E21B 47/122* (2013.01); *G01N 2203/0688* (2013.01); *G01V 99/00* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | | |
|---|---|---|---|---|
| 3,237,448 | A * | 3/1966 | Howell .................... | G01K 3/04 374/E3.004 |
| 3,250,901 | A * | 5/1966 | Brahm .................... | G01K 1/022 374/103 |
| 3,362,217 | A * | 1/1968 | Rush ........................ | G01K 3/04 374/E3.004 |
| 4,135,246 | A * | 1/1979 | McMannis ............... | G07C 3/00 701/100 |
| 4,575,803 | A * | 3/1986 | Moore .................... | F01D 21/00 346/33 TP |
| 4,787,053 | A * | 11/1988 | Moore .................... | F01D 21/00 340/945 |

(Continued)

FOREIGN PATENT DOCUMENTS

| | | |
|---|---|---|
| EP | 0 509 817 A1 | 10/1992 |
| WO | 02-38915 | 5/2002 |

OTHER PUBLICATIONS

International Search Report from PCT/GB2010/002202 issued on Apr. 10, 2011.

(Continued)

*Primary Examiner* — Edward Cosimano

(57) ABSTRACT

Apparatus for calculating service life expectancy of wellbore intervention tools comprising one or more sensors, power means, control means and wireless connectivity means. Also a method of the measuring and calculating the service life expectancy of wellbore intervention tools using this apparatus.

20 Claims, 2 Drawing Sheets

(56) References Cited

U.S. PATENT DOCUMENTS

| | | | | |
|---|---|---|---|---|
| 5,033,010 A | * | 7/1991 | Lawrence | G05B 23/0264 346/33 TP |
| 6,659,174 B2 | * | 12/2003 | Hogan | E21B 43/128 166/250.01 |
| 7,373,975 B2 | * | 5/2008 | Dion | E21B 47/124 166/250.01 |
| 7,925,454 B1 | * | 4/2011 | Narcus | G01D 21/00 340/679 |
| 2002/0130783 A1 | | 9/2002 | Hogan | |
| 2006/0085134 A1 | | 4/2006 | Dion et al. | |
| 2006/0238161 A1 | | 10/2006 | Rusnell et al. | |

OTHER PUBLICATIONS

Great Britain Search Report from GB0921340.6 issued on Jan. 20, 2011.

* cited by examiner

TOOL SERVICE LIFE SENSOR WITH WIRELESS CONNECTIVITY

BACKGROUND OF THE INVENTION

Field of the Invention

The present invention relates generally to a method and apparatus to keep track of the service life expectancy of wellbore intervention tools, and more particularly to an autonomous apparatus that is intended to follow the use and exposure of a wellbore intervention tool while continuously calculating a prediction of the remaining life expectancy of the tool monitored.

The tool service life is a percentage number and is based on a generic set of algorithms characterizing the influential failure-mechanisms verses exposure, workload, and time. The Tool Service Life Sensor ("TSLS") is provided with wireless connectivity and may be interrogated in the well or at the surface. Upon interrogation, the TSLS will prompt the mission, the life expectancy left, tool identity and status, as well as particular events (above certain expectation limits). The TSLS may be integrated and be incorporated as part of a downhole intervention tool or it may have its own housing.

For those skilled in the art, this is not the downhole-tool version and substitution for an airplane "flight recorder" or "black box," but a mission recorder telling the operator the status of the tool and how much future or "usable" life expectancy the tool provides. This is calculated and expressed directly by the TSLS in percentage design life left, and is based on historic (recorded) use. Further, it is an estimate of how many hours of use the life expectancy prediction represents. Secondarily, but just as importantly, the TSLS provides as output information the occurrence of damage-events as recorded outside a defined level.

U.S. Patent Application Publication No. 2006/0238161 A1, to Rusnell et al., describes a system that records the use versus load with time. This invention is intended for attachment to rental equipment in order to manage their charges and service. The latter is related to the use and workload recorded. This invention does not have the mission, or the ability, to predict the remaining "life" of a tool. Further, it does not include wireless connectivity, which in many applications is required as the tool and the TSLS target may be located in a remote location, non-accessible with a cable connection.

U.S. Patent Application Publication No. 2006/0085134 A1, to Dion et al., is a downhole memory recorder to be used in a well to record the usage of a tool. Operating data collected as well as peak conditions from the recorder are downloaded and used to evaluate the life and status of the mission tool in a surface database. This unit is not autonomous and does not on its own calculate the remaining life of a mission tool.

SUMMARY OF THE INVENTION

By the present invention all decisions and calculations of expected lifetime and occurrence are performed by sets of static algorithms describing the governing failure mechanisms considering the life of the unit verses time, load, use, and/or exposure, of which magnitude and impact are measured by an application-specific parametric sensor array of the TSLS. Consequently, lifetime prediction of this invention is static as described, and not a process based on human resources evaluating data records like those described in previous art.

According to the present invention, there is provided apparatus for calculating service life expectancy of wellbore intervention tools, the apparatus comprising one or more sensors, power means, control means, and wireless connectivity means. The application also provides a method for measuring the service life expectancy of wellbore intervention tools, in which apparatus according to the present invention is positioned in a wellbore adjacent to or near a tool to be monitored, measuring one or more physical properties with the one or more sensors in the apparatus, recording and processing the data obtained from the sensors, and calculating the expected life of the tool being monitored using the data collected. Preferred and optional features of the apparatus and method of the present invention will be clear from the accompanying claims and from the detailed description of an embodiment which follows.

All wellbore equipment has a certain life expectancy that is generally based on technology, material properties, ruggedness, and compatibility, to mention a few non-limiting parameters. Any use of a tool in a well will induce wear on the parts of which it consists. The wear may be categorized and broken down into segments of, for example, wear and tear, all of which may be calculated based on environment, material properties, function, and exposure. Further, in any tool there will be functions or components that are likely to wear out and fail before others due to the nature of the tool and its parts, as well as the technology utilized. Consequently, such a parameter or parameters will be the life-limiting factors of the tool and the governing factors for the service and work-over to proceed.

For the purpose of the invention, the governing life-limiting parameters are referred to herein as the "apparent failure mechanisms of the tool." Further, and for the continuation of this process, the governing failure mechanisms of a mission intervention tool will be the criteria to calculate and predict its lifetime expectancy. Consequently, in general, all failure mechanisms may be characterized and their influence on the tool total life expectancy may be predicted based on use, workload, and time. Further, the use may be categorized as heavy or light and be dependent on which parameter and load that a user selects to distinguish between the two. Again, the outcome is a predictable reduction of a mission or tool service-life.

This apparatus is by definition a generic type "Tool Service Life Sensor" and will prompt the user with the status of the tool and how much more use it will take before it is to be taken out of service for overhaul or replacement. The life expectancy is calculated based on how many of the required number of algorithms that characterize the governing failure mechanisms upon which the tool-life is based and what physical property parameters or work-load are associated with them. The calculation of the tool life is in turn linked to integral sensor of the apparatus that is sequentially recorded to memory on each event and by time.

DESCRIPTION OF THE DRAWINGS

Referring now to the drawings, wherein like elements are numbered alike in the several FIGS..

DETAILED DESCRIPTION OF THE PREFERRED EMBODIMENT

Figure 1:
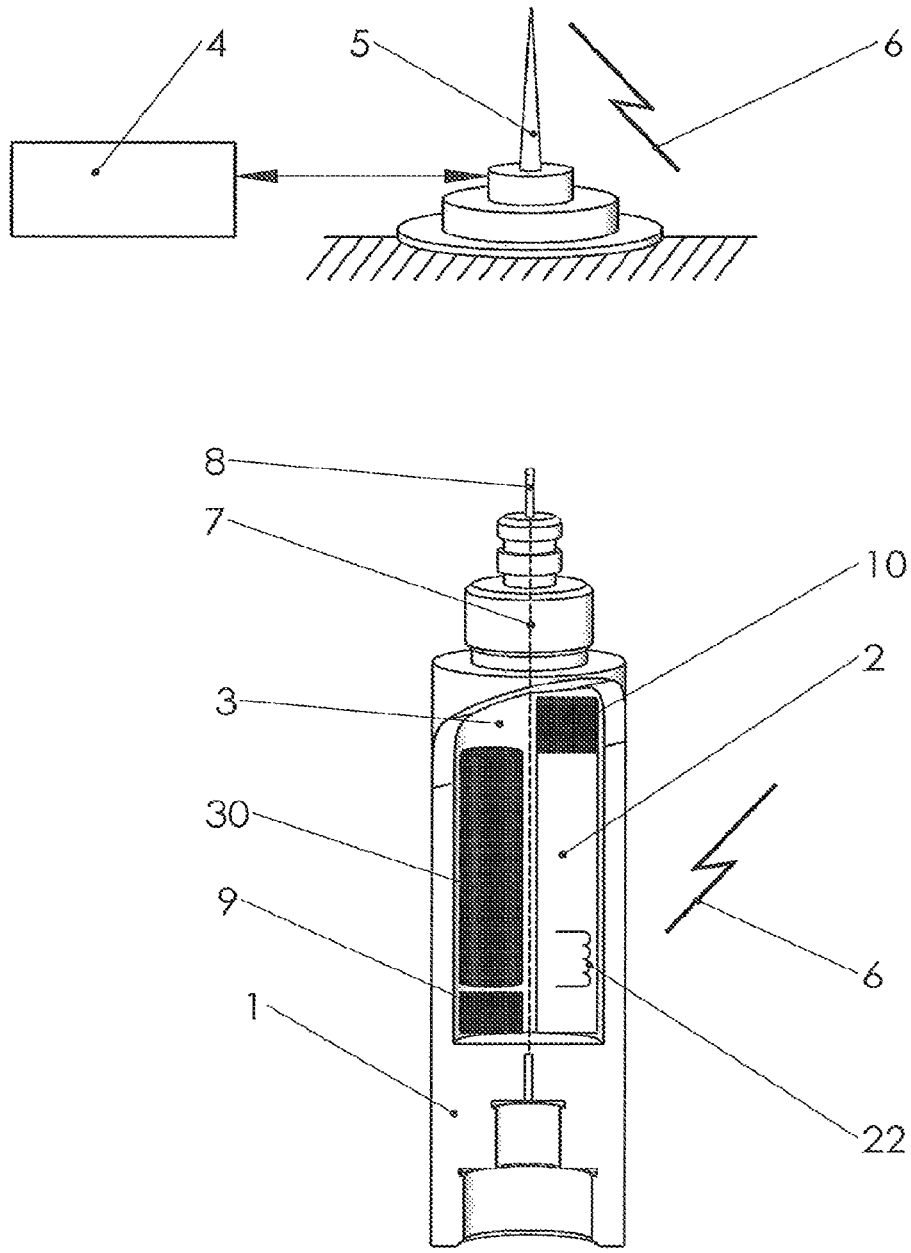
FIG. 1 shows an outline schematic of the Tool Service Life Sensor ("TSLS") with its major components.
Figure 2:
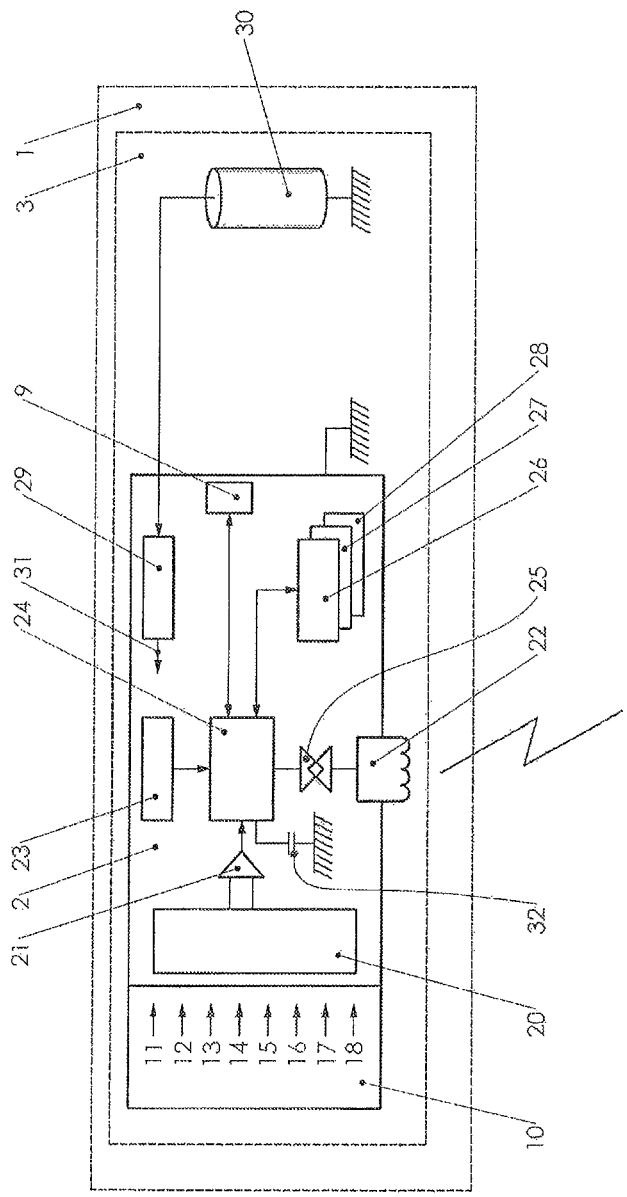
FIG. 2 is a diagrammatic block diagram illustrating the electrical and functional configuration of the TSLS.

A first embodiment of the Tool Service Life Sensor ("TSLS") and associated equipment are shown in FIG. 1 and FIG. 2. Referring to FIG. 1, a typical embodiment of the TSLS is illustrated. A housing 1 holds a main frame 3 containing components for the TSLS. The main frame 3 hosts a battery 30, a sensor package 10, a controller/recorder board 2, an electromagnetic antenna 22, and a wired connectivity element 9. For practical means, the housing 1 provides an electrical feedthrough 8 for the operation of and connection to tools operated electrically. Finally, the housing 3 is provided with a threaded seal connection 7 for attaching to a mission tool (not shown).

The TSLS 3 communicate wirelessly to a remote link 5 which is controlled by a controller/computer device 4. The controller/computer device 4 may be a traditional PC computer running a software application to interrogate the TSLS. Wireless connectivity between the units is indicated by the reference numeral 6. The wireless connectivity 6 is through electromagnetic means and is functional in air at the surface and in fluids or gas which may be present in the wellbore.

Referring to FIG. 2, a functional block diagram of the TSLS is shown. The first building block is the sensor package 10. The sensor package 10 may consist of one or more sensors 11, 12, 13, 14, 15, 16, 17, 18, etc. The sensors may measure properties selected from the following non-limiting list: temperature, temperature difference, pressure, differential pressure, vibration, chock, electric field, magnetic field, acceleration, load, displacement means, acoustic type, resistivity, relative humidity, thermal conductivity, pH, electrical potential AC/DC, electrical current AC/DC, tension, compression, torque, shear force, inclination, magnetic orientation, toolface, gravity, flow, turbidity, density, displacement, dimension, radiation, speed, frequency, weight, buoyancy, ratiometric type, electrical event type, as well as ambient conditions inside the housing 1. The sensor package 10 may consist of one or more sensors, or a combination of one or more of all sensors listed.

Input signals from the sensor package 10 is multiplexed by a multiplexer 20 and is amplified/linearized accordingly by an amplifier section 21. In turn, the output of the amplifier section 21 is fed to a controller 24 for acquisition. Due to the wide temperature operating range of the TSLS, the data acquisition is provided with a stable reference 32 for signal processing and comparison.

The TSLS is powered by the battery 30 and provides a stable output to a power supply 29. The power supply 29 has a power supply output 31 which is the main electric source for the circuits and sensors of the TSLS. To keep track of time the controller 24 is connected to a timer or clock device 23 which is a stable time source to keep track of time even at elevated conditions. For those skilled in electronic arts, the times or clock device 23 of the TSLS may be a doubly rotated SC (SC=Sensitivity Cut) quartz crystal resonator. The TSLS is autonomous, and executes a program application set up and managed by the controller 24. The program application is user defined, and is based upon analysis of the failure mechanisms of the mission element tool. Data processed and events recorded are stored in memory sections 26, 27, and 28. The memory technology used may be any volatile or non-volatile type.

Connectivity is provided by a modem 25 and the electromagnetic antenna 22. The TSLS also provides the wired connectivity 9 which may be used for hardwired communication where practical.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

The invention claimed is:

1. An apparatus for calculating the service life expectancy of wellbore intervention tools, the apparatus comprising:
   one or more sensors for measuring physical properties associated with the operation of at least one wellbore intervention tool;
   a controller located at or near the location of the one or more sensors for acquiring data from the one or more sensors indicative of the occurrence of events associated with the operation of at least one wellbore intervention tool and time information associated with the events;
   a power supply for powering the controller;
   a control device located remotely from the controller and the one or more sensors; and
   connectivity apparatus facilitating communication between the controller and the control device;
   wherein at least of the controller and the control device evaluates the data from the one or more sensors indicative of the occurrence of events associated with the operation of at least one wellbore intervention tool and time information associated with the events to provide a prediction of reduction remaining wellbore intervention tool service-life.

2. An Apparatus as defined in claim 1, further comprising:
   a recorder for storing the data from the one or more sensors indicative of the occurrence of events associated with the operation of at least one wellbore intervention tool and time information associated with the events until they are provided by the controller to the control device.

3. An Apparatus as defined in claim 1, wherein the connectivity apparatus provides wireless connectivity and comprises:
   apparatus located at each of the controller and the control device for providing electromagnetic communication therebetween.

4. An Apparatus as defined in claim 1, wherein the control device comprises:
   a computer running a software application to interrogate the controller and provide the prediction of reduction remaining mission or tool service-life.

5. An Apparatus as defined in claim 1, wherein the connectivity apparatus provides wired connectivity and comprises:
   apparatus located at each of the controller and the control device and therebetween for providing wired connectivity between the controller and the control device.

6. An Apparatus as defined in claim 1, further comprising:
   a multiplexer located between the one or more sensors and the recorder.

7. An Apparatus as defined in claim 6, further comprising:
   an amplifier located between the multiplexer and the recorder.

8. An Apparatus as defined in claim 1, further comprising:
a timer or clock device that keeps track of time and enables the generation of data indicative of time information associated with the events.

9. An Apparatus as defined in claim 8, wherein the timer or clock device comprises:
a doubly rotated sensitivity cut quartz crystal resonator.

10. An Apparatus as defined in claim 1, wherein the one or more sensors, the controller, and the power supply are housed within a housing.

11. An Apparatus as defined in claim 10, wherein the housing provides an electrical feedthrough to facilitate the operation of the one or more sensors and the controller.

12. An Apparatus as defined in claim 1, wherein the one or more sensors measure one or more properties selected from the group consisting of:
temperature, temperature difference, pressure, differential pressure, vibration, chock, electric field, magnetic field, acceleration, load, displacement means, acoustic type, resistivity, relative humidity, thermal conductivity, pH, electrical potential ac/dc, AC/DC, electrical current AC/DC, tension, compression, torque, sheer force, inclination, magnetic orientation, tool face, gravity, flow, turbidity, density, displacement, dimension, radiation, speed, frequency, weight, buoyancy, ratiometric type, electrical event type, and ambient conditions.

13. An Apparatus as defined in claim 12, wherein at least one of the one or more sensors is capable of measuring one or more of the selected properties.

14. A method for measuring the service life expectancy of wellbore intervention tools using the apparatus defined in claim 1; comprising:
positioning the one or more sensors, the controller, and the power supply in a wellbore adjacent to or near a wellbore intervention tool to be monitored;
measuring one or more physical properties of the wellbore intervention tool with the one or more sensors;
recording and processing the data obtained from the one or more sensors indicative of the occurrence of events associated with the operation of at least one wellbore intervention tool; and
calculating the expected life of the wellbore intervention tool being monitored using the data obtained.

15. A method as defined in claim 14, in which the calculating step identifies a first component or components of the wellbore intervention tool which are expected to wear out and bases the life expectancy of the tool thereupon.

16. A method as defined in claim 14, in which the calculating step considers one or more parameters from the group comprising:
the time that the wellbore intervention tool is used, the load of the wellbore intervention tool, the operational use of the wellbore intervention tool, and the exposure of the wellbore intervention tool.

17. A method as defined in claim 16, in which the parameters used in the calculating step further comprise:
the material properties of the wellbore intervention tool, the ruggedness of the wellbore intervention tool, and the compatibility with the environment of the wellbore intervention tool.

18. An apparatus for calculating the service life expectancy of a wellbore tool, the apparatus comprising:
at least one sensor for measuring a physical property associated with the operation of a wellbore tool;
a controller the acquires data from the at least one sensor indicative of the occurrence of events associated with the operation of the wellbore tool and time information associated with such events and records the data;
a power supply for powering the controller;
a control device located remotely from the controller and the at least one sensor; and
a communication link between the controller and the control device;
wherein the control device is configured to evaluate the data to predict the remaining service-life of the wellbore tool.

19. An apparatus as defined in claim 18, wherein the evaluation of the data to predict the remaining service-life of the wellbore tool is performed by the control device by running a software application to interrogate the controller and provide the prediction of reduction remaining mission or tool service-life.

20. A method for calculating the service life expectancy of a wellbore tool, comprising:
measuring a physical property associated with the operation of a wellbore tool with at least one sensor;
acquiring and recording data from the at least one sensor indicative of the occurrence of events associated with the operation of the wellbore tool and time information associated with such events with a controller;
providing the data from the controller to a control device located remotely from the controller and the at least one sensor; and
evaluating the data with the control device to predict the remaining service-life of the wellbore tool.

* * * * *